United States Patent [19]
Ueno et al.

[11] Patent Number: 5,317,032
[45] Date of Patent: May 31, 1994

[54] PROSTAGLANDIN CATHARTIC

[75] Inventors: Ryuzo Ueno; Ryuji Ueno, both of Nishinomiya; Sachiko Kuno, Takarazuka; Tomio Oda, Itami, all of Japan

[73] Assignee: Kabushiki Kaisha Ueno Seiyaku Oyo Kenkyujo, Osaka, Japan

[21] Appl. No.: 996,495

[22] Filed: Dec. 30, 1992

Related U.S. Application Data

[63] Continuation of Ser. No. 713,603, Jun. 11, 1991, abandoned, which is a continuation of Ser. No. 501,348, Mar. 28, 1990, abandoned, which is a continuation-in-part of Ser. No. 252,467, Oct. 3, 1988, abandoned.

[30] Foreign Application Priority Data

Oct. 2, 1987 [JP] Japan ................. 62-250163

[51] Int. Cl.$^5$ ............................. A61K 31/557
[52] U.S. Cl. ................. 514/530; 514/573; 560/121; 562/503
[58] Field of Search ............... 514/530, 573

[56] References Cited

U.S. PATENT DOCUMENTS

| | | | |
|---|---|---|---|
| 4,163,016 | 7/1979 | Holland et al. | 560/121 |
| 4,212,993 | 7/1980 | Holland et al. | 560/121 |
| 4,260,818 | 4/1981 | Holland et al. | 560/121 |
| 4,306,078 | 12/1981 | Holland | 562/503 |
| 4,374,856 | 2/1983 | Ruwart | 560/121 |
| 4,410,720 | 10/1983 | Holland | 560/121 |
| 5,166,178 | 11/1992 | Veno | 514/573 |

FOREIGN PATENT DOCUMENTS 0000207 1/1979 European Pat. Off. .
2146325 4/1985 United Kingdom .

OTHER PUBLICATIONS

Robert, et al., "Enteropooling Assay: A Test for Diarrhea Produced by Prostaglandins", Prostaglandin, May 1986, vol. 11, No. 5, p. 809.

10th Annual Meeting of Nippon Ensho Gakkai (Jul. 20-21 1989), Abstract of "Effects of Lipo-PGE$_1$ on Renal Diseases: On and Around the Effect on Creatinine Clearance (Ccr)."

Zurier, et al., "Prostaglandin E$_1$ Treatment of NZB/NZW Mice", Arthritis and Rheumatism, vol. 20, No. 2 (Mar. 1977) p. 723.

*Primary Examiner*—Robert Gerstl
*Attorney, Agent, or Firm*—Sughrue, Mion, Zinn, Macpeak & Seas

[57] ABSTRACT

The present invention relates to cathartics comprising 15-keto-16-halogen-PGs as an essential ingredient without substantive side-effects; the catharic effect is thought mainly caused by an enteropooling effect.

7 Claims, No Drawings

PROSTAGLANDIN CATHARTIC

This is a continuation of application Ser. No. 07/713,603 filed Jun. 11, 1991, in turn a continuation of Ser. No. 07/501,348 filed Mar. 28, 1990, in turn a continuation-in-part application of application Ser. No. 07/252,467 filed Oct. 3, 1988 all now abandoned.

BACKGROUND OF THE INVENTION

The present invention relates to cathartics which contain derivatives of prostaglandins.

Prostaglandins (hereinafter referred to as PGs) is the name of the group of fatty acids which possess various physiological activities and contained in human and animal tissues and organs. PGs basically contain the prostanoic acid skeleton of the following formula:

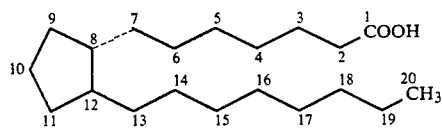

and some synthetic products may contain the above skeleton with some modification.

PGs are classified into several types according to the structure and substituents on the five-membered ring, for example,

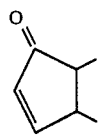

Prostaglandins of the A series (PGAs):

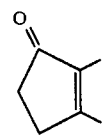

Prostaglandins of the B series (PGBs):

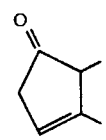

Prostaglandins of the C series (PGCs):

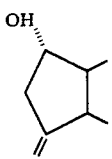

Prostaglandins of the D series (PGDs):

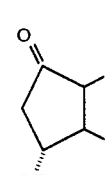

Prostaglandins of the E series (PGEs):

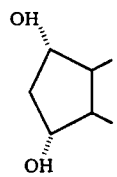

Prostaglandins of the F series (PGFs):

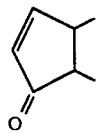

Prostaglandins of the J series (PGJs):

and the like. Further, they are classified into $PG_1s$ containing a 5,6-single bond:

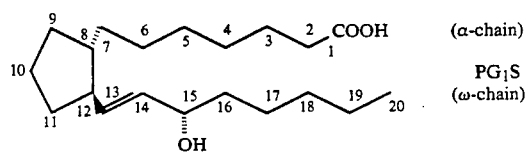

$PG_2s$ containing, a 5,6-double bond:

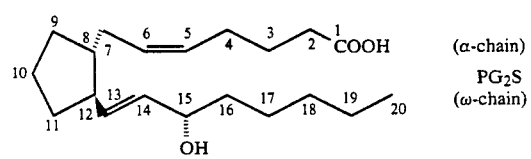

and $PG_3s$ containing 5,6- and 17,18-double bonds:

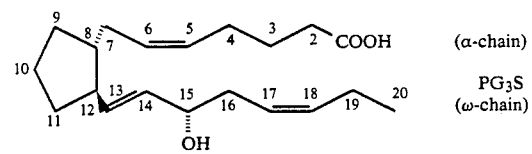

PGs are known to have various pharmacological and physiological activities, for example, vasodilation, inducing of inflammation, platelet aggregation, stimulating uterine muscle, stimulating intestinal muscle, antiulcer effect and the like.

On the other hand, PGs having a 13,14-single bond and a C-15 constituting carbonyl group, and those having a 13,14-double bond and a C-15 constituting carbonyl group are found to exist in human or animal metabolites. These 13,14-dihydro-15-keto-prostaglandins and 15-keto-prostaglandins (hereinafter referred to as 15-keto-PGs) are known to be naturally produced metabolites by enzymatic metabolism of the corresponding PGs in vivo. These 15-keto-PGs have been reported to hardly exhibit various physiological activities that PGs possess and be pharmacologically and physiologically inactive metabolites [see, Acta Physiologica Scandinavica, 66, p.509- (1966)].

While estimating the pharmacological activities of the derivatives of 15-keto-PGs, however, the present inventors have found the derivatives substituted by one or more halogen atoms at the C-16 position, especially, fluorine atoms cause strong cathartic effect according to enteropooling test and the like, and have attained the present invention.

SUMMARY OF THE INVENTION

Present invention relates to cathartics comprising 15-keto-16-halogen-PGs without substantive side effects such as stomachache caused by intestinal contraction.

Accordingly, 15-keto-16-halogen-PGs of the present invention may be used for treatment or prevention of constipation as well as to effect loose bowels in the patients suffering from disease in hernia or cardiovascular system in order not to strain at stool, or suffering from proctogenic diseases. Moreover, they may be used to empty the intestine before inspection or operation, or to wash out harmful substances from intestine in case of drug or food poisoning.

DETAILED DESCRIPTION OF THE INVENTION

The present invention provides cathartics containing 15-keto-16-halogen-prostaglandins (hereinafter referred to as 15-keto-16-halogen-PGs) as active ingredients.

In this description, 15-keto-PGs are expressed as follows. That is, in 15-keto-PGs, the carbons constituting an α-chain, a ω-chain and a five-membered ring are numbered according to the basic skeleton as follows:

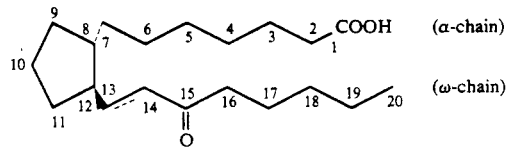

That is, in the basic skeleton, the constituent carbon atoms are numbered in such a way that the carbon atom in the carboxyl group is C-1, and the α-chain contains C-2 - C-7, the number increasing toward the ring, the five-membered ring contains C-8 - C-12, and the ω-chain contains C-13 - C-20. When the carbons of α-chain are fewer, the numbers of the carbon atoms ensuing C-2 should be properly shifted, and when more than 7, the compound is named provided that carbon at the C-2 position has substituent instead of carboxyl group (at the C-1 position). When the ω-chain contains fewer carbon atoms they should be numbered correspondingly smaller than 20, and when more than 8, the carbon atoms at the 21 position and thereafter should be regarded as a substituent. As configuration, it is considered according to that of the above essential skeleton unless otherwise described.

For example, PGD, PGE and PGF mean compounds having hydroxyl group at the C-9 and/or C-11 positions. In the present invention, PGs also include those having other group instead of the hydroxyl group on the C-9 and/or C-11 positions, they being named as 9-dehydroxy-9-substituted or 11-dehydroxy-11-substituted compounds.

15-keto-PGs used in the present invention may be PGs wherein the carbon atom at the C-15 position forms carbonyl group. Accordingly, any of 15-keto-PG$_1$s containing a 5,6-single bond, 15-keto-PG$_2$s containing a 5,6-double bond, 15-keto-PG$_3$s containing both 5,6- and 17,18-double bonds may be used.

That is, 15-keto-16-halogen-PGs used in the present invention may contain at least one or more halogen atoms, particularly, one or more fluorine atoms at the C-16 position, neglecting the structure and substituents on the five-membered ring, or the existence of a double bond or other substituents.

In general, cathartics may be roughly classified into aperients and drastics according to the difference of the effect, the former effecting discharge of loose feces while the latter purging watery feces.

Cathartics work by the combination of one or more of the three mechanisms shown below, thereby increasing water content of feces and promoting transfer of the content in the intestines:

(i) Water and electrolytes may be kept in intestines owing to the hydrophilicity or osmotic pressure of the drug, thereby the intraintestinal content increased in volume which indirectly results in faster transfer thereof.

(ii) The drug may work on the intestinal mucosa to reduce total amount of normal absorption of electrolytes and water and increase the amount of water, indirectly resulting in faster transfer of the intraintestinal content.

(iii) The drug firstly works on intestinal movement to fasten transfer, indirectly resulting in reduced net absorption of water and electrolytes because the time for them to be absorbed is reduced.

The enteropooling test employed in the present invention is intended to investigate mainly on the action (ii), which assesses the effect of the drug on the intraintestinal water pool by measuring the volume of the intraintestinal content. 15-keto-16-halogen-PGs of the present invention may show extremely great enteropooling effect. However, they hardly or slightly cause contraction of intestines which is one of indexes for assessment of the action (iii). Accordingly, 15-keto-16-halogen-PGs of the present invention are considered to induce diarrhea by mainly acting on intestinal mucosa directly or indirectly to affect transfer of electrolytes and water from intestinal walls into blood vessels, resulting in reduced water absorption through the intestines, increased intraintestinal water pool and promoted transfer of the intraintestinal content.

15-Keto-16-halogen-PGs used in the present invention may be salts or those with an esterified carboxyl group. Such salts include physiologically acceptable salts, for example, those of alkali metals such as sodium, potassium; those of alkaline earth metals such as calcium, magnesium; those of physiologically acceptable ammonium salts such as ammonia, methylamine, dimethylamine, cyclopentylamine, benzylamine, piperidine, monoethanolamine, diethanolamine, monomethylmonoethanolamine, tromethamine, lysine, tetralkylammonium salt and the like. Such esters include, for example, straight or branched alkyl esters which may contain one or more unsaturated bonds such as methyl, ethyl, propyl, butyl, isopropyl, t-butyl, 2-ethylhexyl ester; esters having an alicyclic group such as a cyclopropyl, cyclopentyl or cyclohexyl group; esters containing an aromatic group such as a benzyl or phenyl group (wherein the aromatic group may contain one or more substituents); a hydroxyalkyl or alkoxyalkyl ester such as a hydroxyethyl, hydroxyisopropyl, polyhydroxyethyl, polyhydroxyisopropyl, methoxyethyl, ethoxyethyl or methoxyisopropyl ester; alkylsilyl esters such as a trimethylsilyl or triethylsilyl ester; or a tetrahydropyranyl ester.

Preferred esters include, for example, straight-chain or branched lower alkyl esters such as methyl, ethyl, propyl, n-butyl, isopropyl or t-butyl ester; a benzyl ester; or hydroxyalkyl esters such as a hydroxyethyl or hydroxyisopropyl ester.

Halogen atoms at the C-16 position includes a fluorine, chlorine or bromine atom. Among them, a fluorine atom is particularly preferred.

The 15-keto-16-halogen-PGs of the present invention may contain one or more unsaturated bond in the basic skeleton. Alternatively, they may be substituted with atoms or groups.

Such unsaturated bond includes, for example, a 2,3-, 5,6- or 17,18-double bond or a 5,6-triple bond. The substituent atom or group includes a halogen atom such as a fluorine, chlorine or bromine atom; an alkyl group such as methyl, ethyl, isopropyl, isopropenyl group; an alkoxy group such as methoxy or ethoxy group; a carbonyl group; a hydroxyl group; a phenyl group; or a phenoxy group. The position of the substituent may not be limited, but the C-3, C-6, C-17, C-19 and/or C-20 position in the basic skeleton may be exemplified. Especially, alkyl group at the C-3, C-17 or C-19 position; a carbonyl group at the C-6 position; an alkyl or alkoxy group at the C-20 position are typical examples.

PGs include the compounds containing a hydroxyl group at the C-9 and/or C-11 position such as PGD, PGE, PGF and the like. In the present description, PGs further include compounds containing a hydroxyalkyl or alkyl group instead of the hydroxyl group at the C-9 and/or C-11 position. As the hydroxyalkyl group, a hydroxymethyl, 1-hydroxyethyl, 2-hydroxyethyl or 1-methyl-1-hydroxyethyl group are preferred. As the alkyl group, a lower alkyl group especially, a methyl or ethyl group and the like are preferred.

The configuration of substituents at the C-9 and/or C-11 position may be α, β or a mixture thereof.

15-keto-16-halogen-PGs of the present invention may include the isomers of the above compounds. Examples of such isomers include keto-hemiacetal tautomers between the hydroxyl group at C-11 position and the carbonyl group at the C-15 position; or optical isomers; geometrical isomers and the like.

The mixture of these isomers, for example, a racemic mixture, tautomers of a hydroxyl compound and a hemiacetal may show similar effect as that shown by the respective compound.

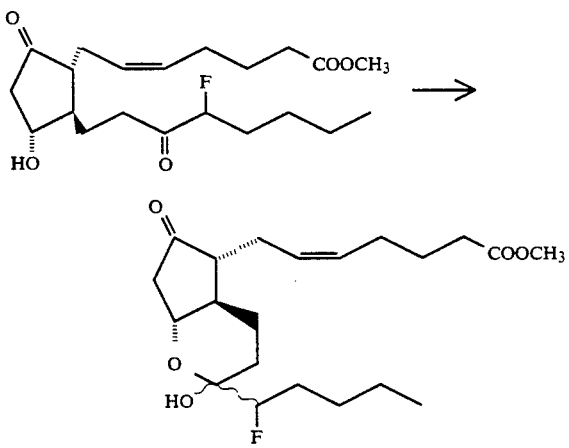

The tautomerism between the hydroxyl group at the C-11 position and the carbonyl group at the C-15 position, shown above, is especially significant in the case of compounds having a 13,14-single bond and a fluorine atom at the C-16 position. These are suggested to existing as a keto-hemiacetal equilibirium mixture.

The above 15-keto-16-halogen-PGs of the present invention may be prepared according to the methods described, for example, in Japanese Patent Application Nos. 18326/1988, 18327/1988 and 108329/1988. These descriptions is incorporated into the present invention.

The 15-keto-16-halogen PGs may prepared according to the following process:

For example, as shown in Preparation Charts, commercially available (−)-Corey lactone, which is used as a starting material, is subjected to Collins oxidation to give an aldehyde. The aldehyde is allowed to react with dimethyl (3-halogen-2-oxoalkyl)phosphonate anion to give α,β-unsaturated ketone and the resultant is reduced to ketone. The carbonyl group of the ketone is allowed to react with a sodium borohydride to give an alcohol and the alcohol is converted to alkyl silyl ether, thereby protected. An alcohol is obtained by ellimination of p-phenylbenzoyl group, and the resulting hydroxyl group is protected using dihydropyran to give a tetrahydropyranyl ether. Thus, precursores of PGs wherein the ω-chain is 13,14-dihydro-15-keto-16-halogen-alkyl can be obtained. Further, the precursors of PGs wherein the ω-chain is 15-keto-16-halogenalkyl may be prepared by proceeding the reaction without reduction of 13,14-double bond of the α,β-unsaturated ketone.

Using the above tetrahydropyranyl ether as a starting material, 6-keto-PG$_1$s of the formula:

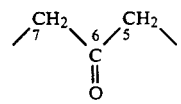

may be obtained as follows: The tetrahydropyranyl ether is reduced using diisobutyl aluminium hydride and the like to give a lactol, which is allowed to react with the ylide obtained from (4-carboxybutyl)triphenylphosphonium bromide, and the resultant is subjected to esterification followed by cyclization, combining the 5,6-double bond and the hydroxyl group at the C-9 position with NBS or iodine, providing a halide. The resultant is subjected to dehydrohalogenation using DBU and the like to give a 6-keto compound. After removal of the silyl ether protecting group at the C-15 position, the resulting alcohol is subjected to Jones oxidation followed by deprotection of tetrahydropyranyl group to give the objective compound.

Further, PG$_2$ of the formula:

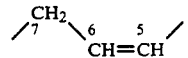

may be obtained as follows: The above tetrahydropyranyl ether is reduced to a lactol, which is allowed to react with the ylide obtained from (4-carboxybutyl)triphenylphosphonium bromide to give a carboxylic acid. The resultant is subjected to esterification. After removal of the silyl ether protecting group at the C-15 position, the resulting alcohol is subjected to Jones oxidation and deprotection of tetrahydropyranyl group to give the objective compound.

In order to obtain PG$_1$s of the formula:

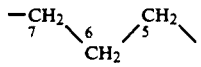

using the above tetrahydropyranyl ether as a starting material, in the same manner as PG$_2$ of the formula:

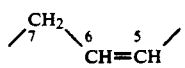

the 5,6-double bond of the resulting compound is subjected to catalytic reduction followed by deprotection. The preparation of 5,6-dehydro-PG$_2$s containing a hydrocarbon chain of the formula:

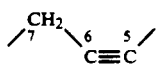

involves 1,4-addition of a monoalkyl copper complex or a dialkyl copper complex of the formula:

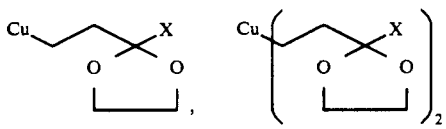

to 4(R) t-butyldimethylsilyloxy-2-cyclopenten-1-one, and trapping the resulting copper enolate with 6-carboalkoxy-1-iodo-2-hexyne or a derivative thereof.

PGs containing a methyl group instead of a hydroxy group at the C-11 position may be obtained as follows: PGA obtained by Jones oxidation of the hydroxy group at the C-9 position of the 11-tosylate is allowed to react with a dimethyl copper complex to give 11-dehydroxy-11-methyl-PGE. Alternatively, an alcohol obtained after elimination of p-phenylbenzoyl group is converted to a tosylate. An unsaturated lactone obtained by DBU treatment of the tosylate is converted to a lactol. After introduction of an α-chain using Wittig reaction, the resulting alcohol (C-9 position) is oxidized to give PGA. PGA is allowed to react with dimethyl copper complex to give 11-dehydroxy-11-methyl-PGE. The resultant is reduced using sodium borohydride and the like to give 11-dehydroxy-11-methyl-PGF.

PGs containing a hydroxymethyl group instead of a hydroxyl group at the C-11 position is obtained as follow: 11-dehydroxy-11-hydroxymethyl-PGE is obtained by a benzophenone-sensitized photoaddition of methanol to PGA. The resultant is, for example, reduced using sodium borohydride to give 11-dehydroxy-11-hydroxymethyl-PGF.

15-Keto-16,16-difluoro-PGs may be obtained using dimethyl(3,3-difluoro-2-oxoalkyl)phosphonate anion in the preparation of α,β-unsaturated ketone.

Alternatively, they may be prepared, for example, according to the description in SYNTHESIS OF DIASTEREOMERIC BIS-UNSATURATED PROSTAGLANDINS [Prostaglandins, 14, P.61–101 (1977)].

The preparations in the present invention are not construed to be limited to them, and suitable means for protection, oxidation, reduction and the like may be employed.

In the 15-keto-16-halogen-PGs used in the present invention, emergency of enteropooling effect may be remarkably enhanced when substituted by at least one halogen atom, especially, fluorine atom at the C-16 position independently of the structure and substituents of the five-membered ring or the existence of the double bonds or other substituents. Especially preferable 15-keto-16-halogen-PGs are those containing a 5,6-double bond or those having the carbon number of 20–22. Another preferable group is the so-called PGE type 15-keto-16-halogen-PGs having a ketone at the C-9 position and a hydroxyl group at the C-11 position in five-membered ring.

In general, PGs are found to possess various pharmacological activities, for example, PGEs or PGFs are found to possess contraction of intestines caused by intestinal stimulation is great, while enteropooling effect is poor. Accordingly, it is impossible to use PGEs or PGFs as cathartics because of side effects such as stomachache caused by the intestinal contraction.

On the other hand, 15-keto-16-halogen-PGs of the present invention may cause extremely great enteropooling effect, inhibiting absorption of water in intestines. Further, the present compound have no or greately reduced, if any, the intestinal contraction effect which PGEs or PGFs may possess. Therefore, the present compound may effect diarrhea without malaise in belly owing to the intestinal contraction, such as bellyache. Moreover, it requires little time to recover from diarrhea symptoms caused by the present compound which possesses great promotion effect of intraintestinal transportation. Therefore, they are very useful as cathartics.

15-keto-16-halogen-PGs of the present invention can be used as remedies for animals and humans, and, in general, used for systemic or local applications by oral administration, or as suppository, enema and the like. Sometimes, they may be applied as intravenous or subcutaneous injection. The dosage varies depending on animals, humans, age, weight, conditions, therapeutic effect, administration route, treatment time and the like. Preferably, it is 0.001–1,000 μg/kg.

The solid composition for oral administration of the present invention includes tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual workup, the composition may contain additives other than inactive diluent, for example, lubricant such as magnesium stearate; disintegrant such as fibrous calcium gluconate; stabilizer such as cyclodextrin, for example, α,β- or γ-cyclodextrin; etherified cyclodextrin such as dimethyl-α-, dimethyl-β-, trimethyl-β- or hydroxypropyl-β-cyclodextrin; branched cyclodextrin such as glucosyl-, maltosyl-cyclodextrin; formylated cyclodextrin, cyclodextrin containing sulfur; mitthoprotol, phospholipid and the like. When the above cyclodextrins are used, inclusion compound with cyclodextrins may be sometimes formed to enhance stability. Alternatively, phospholipid may be sometimes used to form liposome, resulting in enhanced stability.

Tablets or pills may be coated with film soluble in the stomach or intestine such as sugar, gelatin, hydroxypropyl cellulose, hydroxypropylmethyl cellulose phthalate as needed. Further, they may be formed as capsules with absorbable substances such as gelatin.

A liquid composition for oral administration may contain pharmaceutically acceptable emulsion, solution, suspension, syrup, elixir as well as generally used inactive diluent, for example, purified water, ethanol, vegetable oil such as olive oil, coconut oil and the like. Such composition may contain, in addition to the inactive diluent, adjuvants such as lubricants and suspensions, sweetening agents, flavoring agents, preservatives and the like. Such liquid compositions may be directly enclosed in soft capsules.

Solutions for parenteral administration, for example, suppository, enema and the like according to the present invention include steril, aqueous or non-aqueous solution, suspension, emulsion, detergent and the like. The aqueous solution and suspension includes, for example, distilled water, physiological saline and Ringer's solution.

The non-aqueous solution and suspension include, for example, propylene glycol, polyethylene glycol, vegetable oil such as olive oil, alcohols such as ethanol, polysorbate and the like. Such composition may contain adjuvants such as preservatives, wetting agent, emulsifier, dispersant and the like.

The present invention will be illustrated in the following examples.

Preparation of 15-keto-16-halogen-prostagrandins

Preparations of 15-keto-16R,S-fluoro-PGE$_2$, 15-keto-16R,S-fluoro-PGE$_2$ methyl ester and 15-keto-16R,S-fluoromethyl ester:

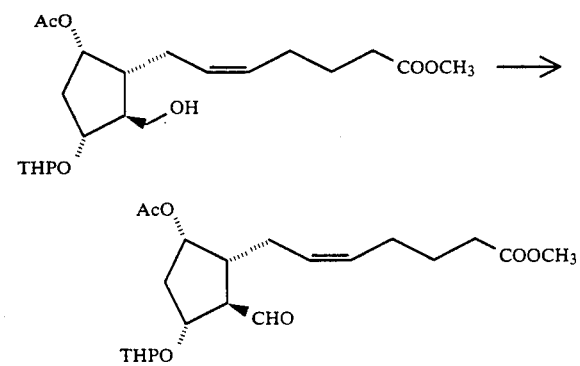

Preparation of methyl (5E)-7R-2R-formyl-3R-(tetrahydropyranyl)oxy-5S-acetoxy-cyclopentyl]-5-heptenate:

Methyl (5E)-7R-[2S-hydroxymethyl-3R-(tetrahydropyranyl)oxy-5S-acetoxy-cyclopentyl]-5-heptenate (0.56 g) was subjected to Collins oxidation (10 eq) in methylene chloride at 0° C. according to the usual way. Sodium bisulfate (15 g) was added to the reaction solution and filtered.

The filtrate was concentrated to give methyl (5E)R-[2R-formyl-3R-(tetrahydropyranyl)oxy-5S-acetoxycyclopentyl]-5-heptenate. Yield; 0.52 g (93%)

Preparation of 9-acetoxy-16R,S-fluoro-15-keto-11-(tetrahydropyranyl)oxy-PGF$_2\alpha$ methyl ester:

Sodium hydride (60%, 0.20 g) and dimethyl(3RS-fluoro-2-oxy-heptyl) phosphonate (1.36 g) were mixed in tetrahydrofuran at room temperature for 10 minutes. A clear solution was obtained. To this solution was added a solution of (5E)-7R-[2R-formyl-3R-(tetrahydro-pyranyl)oxy-5S-acetoxy-cyclopentyl]-5S-heptenate (0.52 g) in tetrahydrofuran, and stirred at 50° C. for 3 hours. Acetic acid (0.30 ml) was added to the reaction mixture, and the crude product obtained after the usual work-up was chromatographed (hexane/ethyl acetate 3:1) to give 9-acetoxy-16R,S-fluoro-15-keto-11-(tetrahydropyranyl)oxy-PGF$_2\alpha$ methyl ester. Yield; 0.54 g (81%)

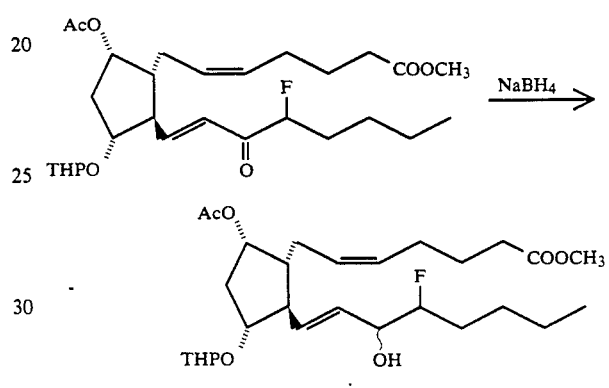

Preparation of 9-acetoxy-16R,S-fluoro-15R,S-hydroxy-11-(tetrahydropyranyl)oxy-PGF$_2\alpha$ methyl ester:

9-Acetoxy-16R,S-fluoro-15-keto-11-(tetrahydropyranyl)oxy-PGF$_2\alpha$ m ethyl ester (0.54 g) was dissolved in methanol, to which was added sodium borohydride (39 mg) at −15° C., and stirred for 30 minutes. The crude product obtained after the usual work-up was chromatographed (hexane/ethyl acetate 2:1) to give 9-acetoxy-16R,S-fluoro-15R,S-hydroxy-11-(tetrahydropyranyl)oxy-PGF$_2\alpha$ methyl ester. Yield; 0.55 g (100%)

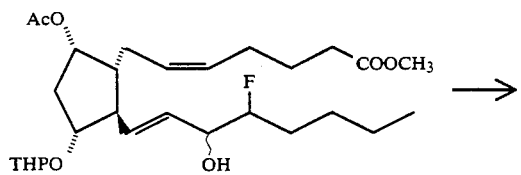

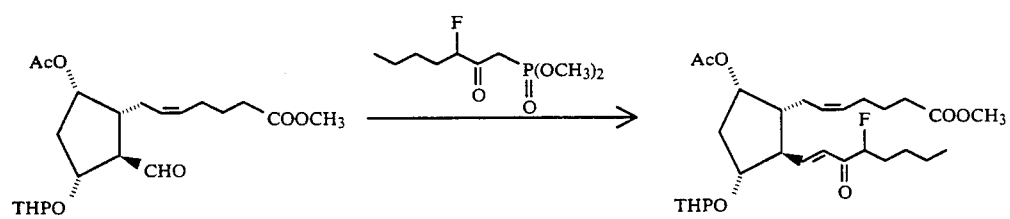

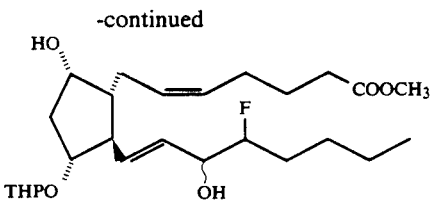

Preparation of 16R,S-fluoro-15R,S-hydroxy-11-(tetrahydropyranyl)oxy-PGF₂α methyl ester:

9-Acetoxy-16R,S-fluoro-15R,S-hydroxy-11-(tetrahydropyranyl)oxy-PGF₂α methyl ester (0.180 g) was dissolved in methanol, to which was added potassium carbonate (0.25 g), and stirred for 7 hours. To the reaction mixture was added acetic acid (0.21 ml), and the crude product obtained after the usual work-up was chromatographed (hexane/ethyl acetate 3:2) to give 16R,S-fluoro-15R,S-hydroxy-11-(tetrahydropyranyloxy)-PGF₂α methyl ester. Yield; 0.139 g (84%)

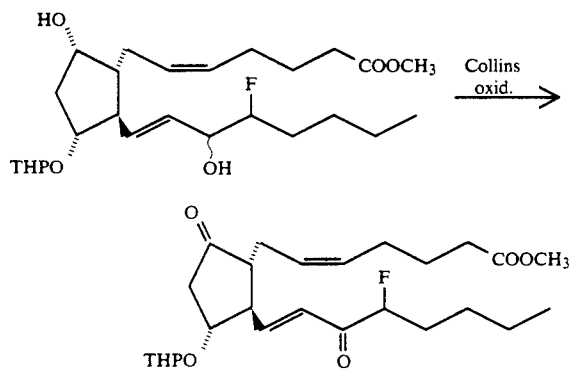

Preparation of 16R,S-fluoro-15-keto-11-(tetrahydropyranyl)oxy-PGE₂ methyl ester:

16R,S-Fluoro-15R,S-hydroxy-11-(tetrahydropyranyl)oxy-PGF₂α methyl ester (0.139 g) was subjected to Collins oxidation (35 eq) in methylene chloride at 0° C. according to the usual way. Sodium bisulfate (6 g) was added to the reaction mixture and filtered. The filtrate was concentrated and chromatographed (hexane/ethyl acetate 2:1) to give 16R,S-fluoro-15-keto-11-(tetrahydropyranyl)oxy-PGE₂ methyl ester. Yield; 0.125 g (91%)

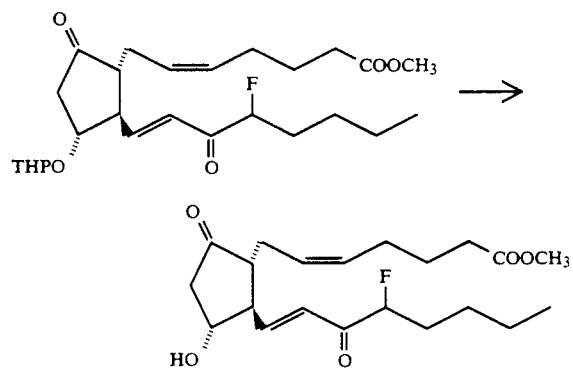

Preparation of 16R,S-fluoro-15-keto-PGE₂ methyl ester:

16R,S-Fluoro-15-keto-11-(tetrahydropyranyl)oxy-PGE₂ methyl ester (0.125 g) was dissolved in a mixtured of acetic acid/THF/water (4:1:2), maintained at 45° C. for 3 hours. Subsequently, the resulting crude product after the usual work-up was chromatographed (benzene/ethyl acetate 1:1) to give 16R,S-fluoro-15-keto-PGE₂ methyl ester. Yield; 0.076 g (74%)

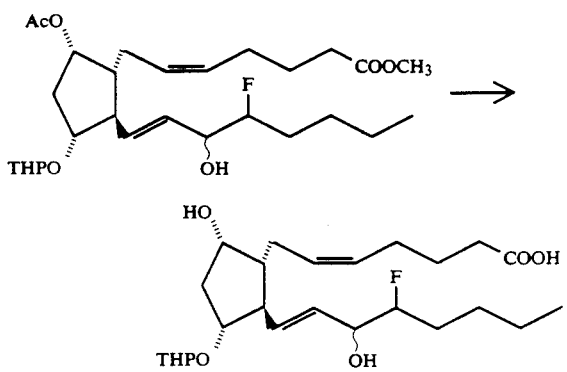

Preparation of 16R,S-fluoro-15R,S-hydroxy-11-(tetrahydropyranyl)oxy-PGF₂α:

9-Acetoxy-16R,S-fluoro-15R,S-hydroxy-11-(tetrahydropyranyl)oxy-PGF₂α methyl ester (0.55 g) was dissolved in a mixture of methanol/1N aqueous solution of sodium hydroxide (2:1) and maintained at room temperature for 3 hours.

After addition of 1N hydrochloric acid followed by the usual work-up, 16R,S-fluoro-15R,S-hydroxy-11-(tetrahydropyranyl)oxy-PGF₂α was obtained. Yield; 0.48 g (98%)

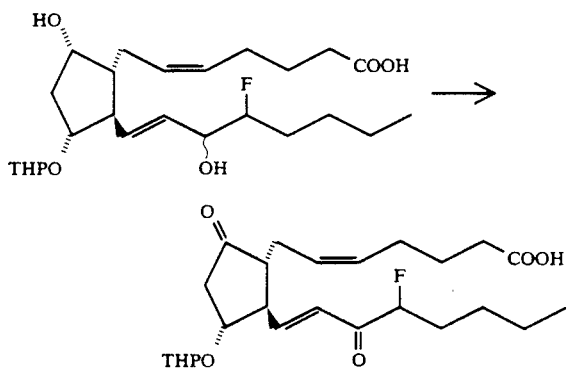

Preparation of 16R,S-fluoro-15-keto-11-(tetrahydropyranyl)oxy-PGE₂:

16R,S-Fluoro-15R,S-hydroxy-11-(tetrahydropyranyl)oxy-PGF₂α (0.48 g) was subjected to Collins oxidation (10 eq) in methylene chloride at room temperature according to the usual way. To the reaction mixture was added sodium bisulfate (15 g) and the resultant was filtered. The filtrate was concentrated and chromatographed (hexane/ethyl acetate 3:1) using silica gel (manufactured by Mallinckrodt; CC-4) to give 16R,S-fluoro-15-keto-11-(tetrahydropyranyl)oxy-PGE₂. Yield; 0.25 g (53%)

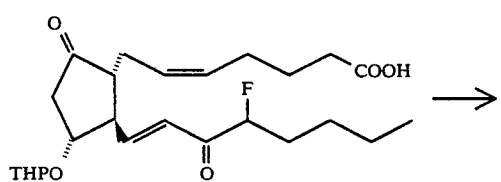

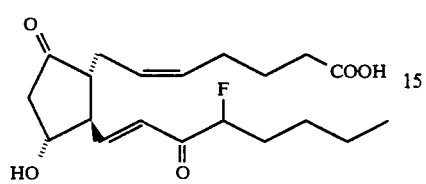

Preparation of 16R,S-fluoro-15-keto-PGE₂:

16R,S-Fluoro-15-keto-11-(tetrahydropyranyl)oxy-PGE₂ (0.25 g) was dissolved in a mixture of acetic acid/THF/water (4:1:2) and maintained at 45° C. for 3 hours.

The crude product obtained after the usual work-up was chromatographed (hexane/ethyl acetate 3.5:1) using silica gel (manufactured by Mallinckrodt; CC-4) to give 16R,S-fluoro-15-keto-PGE₂. Yield; 0.166 g (82%)

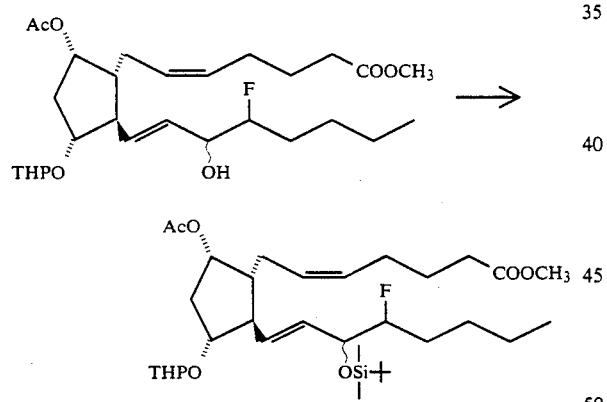

Preparation of 9-acetoxy-15R,S-(t-butyldimethylsiloxy)-16R,S-fluoro-11-(tetrahydropyranyl)oxy-PGF₂α methyl ester:

9-Acetoxy-16R,S-fluoro-15R,S-hydroxy-11-(tetrahydropyranyl)oxy-PGF₂α methyl ester (0.356 g) was dissolved in dimethylformamide, t-butyldimethylsilyl chloride (0.31 g) and imidazole (0.28 g) were added thereto, and the resultant was stirred overnight. The crude product obtained after the usual work-up was chromatographed (hexane/ethyl acetate 4:1) to give 9-acetoxy-15R,S-(t-butyldimethylsiloxy)-16R,S-fluoro-11-(tetrahydropyranyl)oxy-PGF₂α methyl ester. Yield; 0.363 g (83.4%)

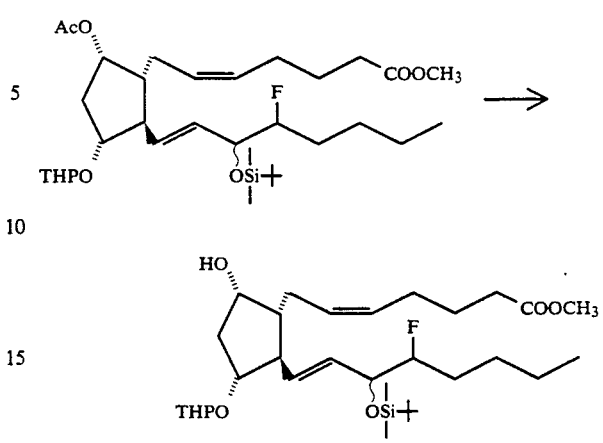

Preparation of 15R,S-(t-butyldimethylsiloxy)-16R,S-fluoro-11-(tetrahydropyranyl)oxy-PGF₂α methyl ester:

9-Acetoxy-15R,S-(t-butyldimethylsiloxy)-16R,S-fluoro-11-(tetrahydropyranyl)oxy-PGF₂α methyl ester (0.363 g) was dissolved in methanol, potassium carbonate (0.32 g) was added thereto, and the resultant was stirred for 7 hours. The crude product obtained after the usual work-up was chromatographed (hexane/ethyl acetate 3:1) to give 15R,S-(t-butyldimethylsiloxy)-16R,S-fluoro-11-(tetrahydropyranyl)oxy-PGF₂α methyl ester. Yield; 0.298 g (88.0%)

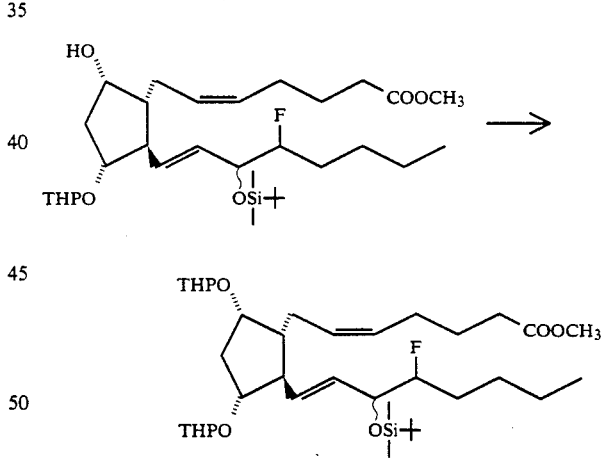

Preparation of 9,11-bis(tetrahydropyranyl)oxy-15R,S-(t-butyldimethylsiloxy)-16R,S-fluoro-PGF₂α methyl ester:

15R,S-(t-Butyldimethylsiloxy)-16R,S-fluoro-11-(tetrahydropyranyl)oxy-PGF₂α methyl ester (0.298 g) was dissolved in methylene chloride, to which were added dihydropyran (1.0 ml) and p-toluenesulfonic acid at 0° C. and stirred for 1 hour. The crude product obtained after the usual work-up was chromatographed (hexane/ethyl acetate 4:1) to give 9,11-bis(tetrahydropyranyl)oxy-15R,S-(t-butyldimethylsiloxy)-16R,S-fluoro-PGF₂α methyl ester. Yield; 0.341 g (100%)

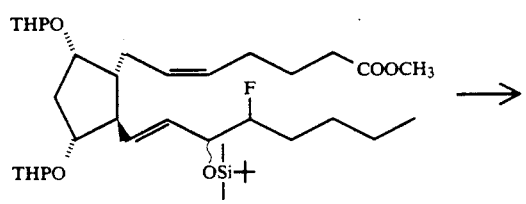

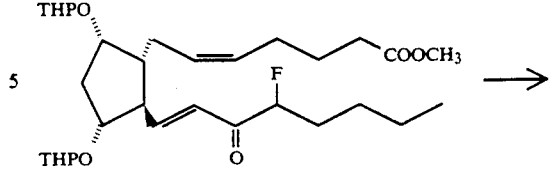

Preparation of 9,11-bis(tetrahydropyranyl)oxy-16R,S-fluoro-15R,S-hydroxy-PGF₂α methyl ester:

9,11-Bis(tetrahydropyranyl)oxy-15R,S-(t-butyldimethylsiloxy)-16R,S-fluoro-PGF₂α methyl ester (0.341 g) was dissolved in tetrahydrofuran, to which was added 1.0M solution of tetrabutylammonium fluoride in tetrahydrofuran (0.75 ml), and the resultant was stirred at 0° C. overnight. The crude product obtained by the usual work-up was chromatographed (hexane/ethyl acetate 2:1) to give 9,11-bis-(tetrahydropyranyl)oxy-16R,S-fluoro-15R,S-hydroxy-PGF₂α methyl ester. Yield; 0.260 g (92.0%)

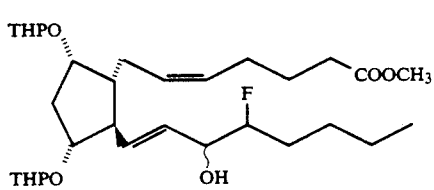

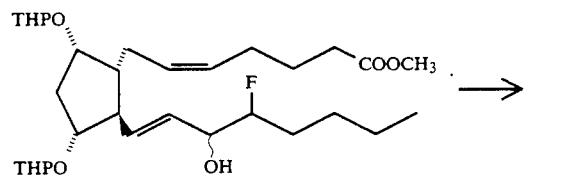

Preparation of 9,11-bis(tetrahydropyranyl)oxy-16R,S-fluoro-15-keto-PGF₂α methyl ester:

9,11-Bis-(tetrahydropyranyl)oxy-16R,S-fluoro-15R,S-hydroxy-PGF₂α methyl ester (0.260 g) was subjected to Collins oxidation (25 eq) in methylene chloride at 0° C. according to the usual way. Sodium bisulfate was added to the reaction solution and filtered. The filtrate was concentrated, and the resulting crude product was chromatographed (hexane/ethyl acetate 4:1) to give 9,11-bis(tetrahydropyranyl)oxy-16R,S-fluoro-15-keto-PGF₂α methyl ester. Yield; 0.245 g (94.6%)

Preparation of 16R,S-fluoro-15-keto-PGF₂α methyl ester:

9,11-Bis(tetrahydropyranyl)oxy-16R,S-fluoro-15-keto-PGF₂α methyl ester (0.245 g) was dissolved in a mixture of acetic acid/THF/water (3:1;1) and maintained at 45° C. for 4 hours. The crude product obtained after the usual work-up was chromatographed (hexane/ethyl acetate 1:2) to give 16R,S-fluoro-15-keto-PGF₂α methyl ester. Yield; 0.148 g (86.8%)

Preparation Chart I

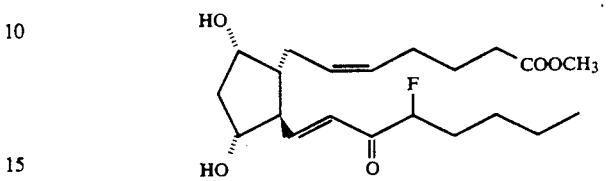

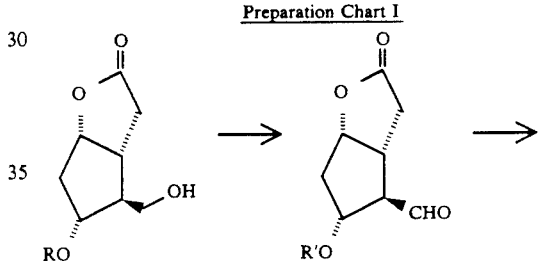

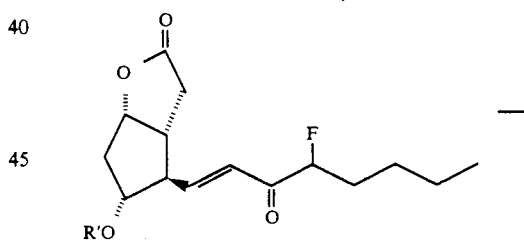

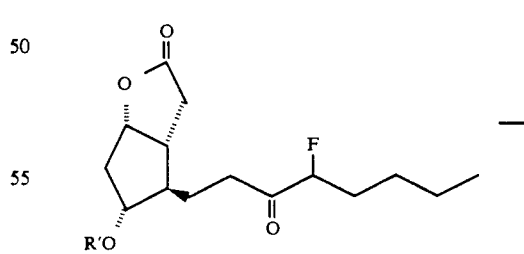

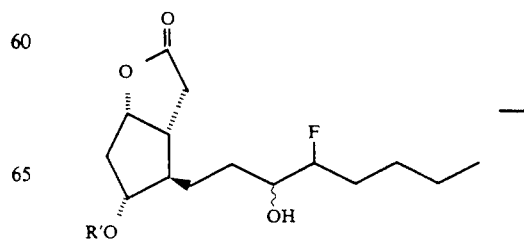

17
-continued
Preparation Chart I
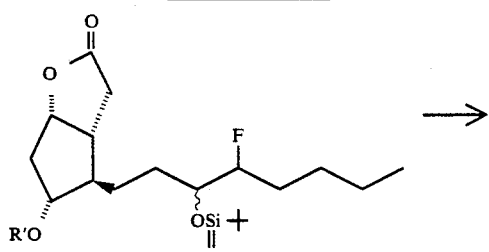
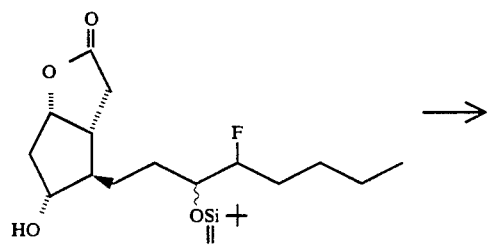
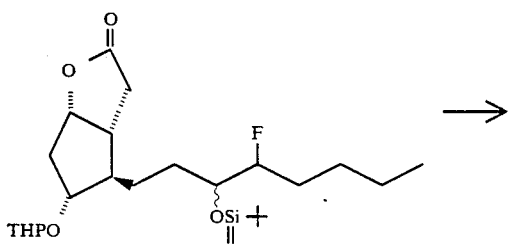
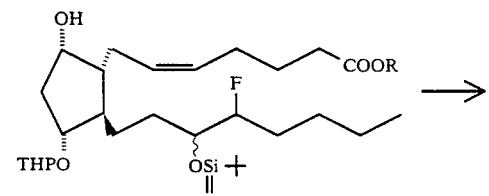
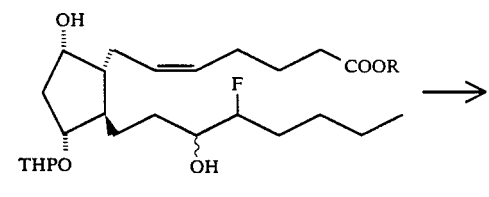
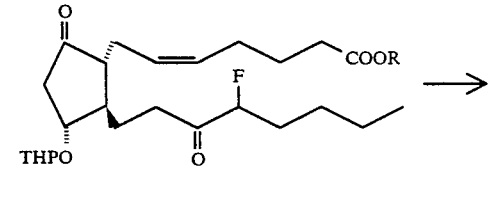
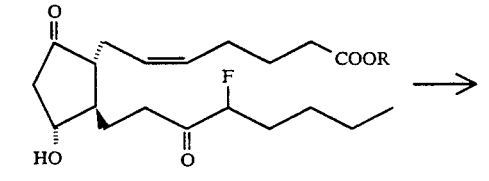
18
-continued
Preparation Chart I
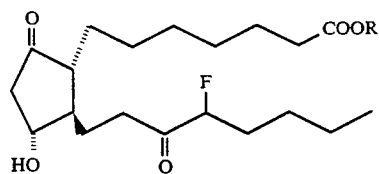
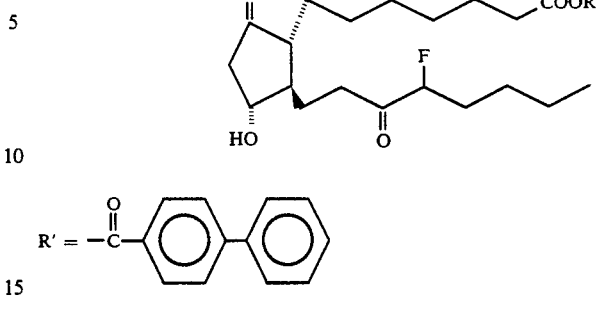
THP = <image with tetrahydropyranyl structure>
Preparation Chart II
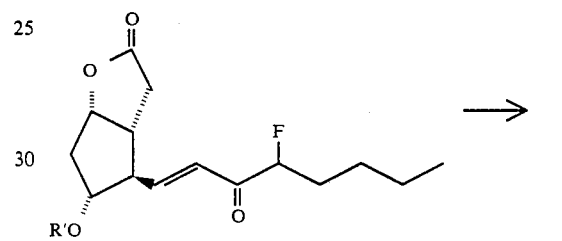
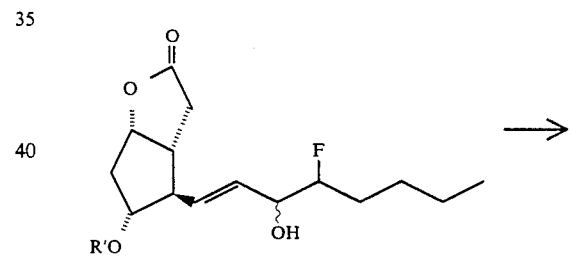
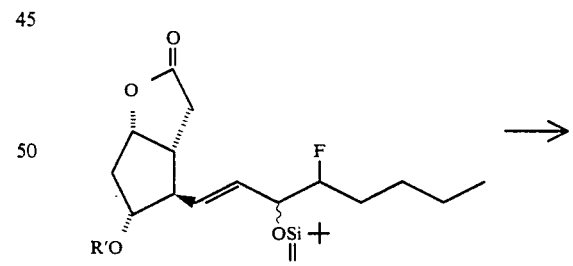
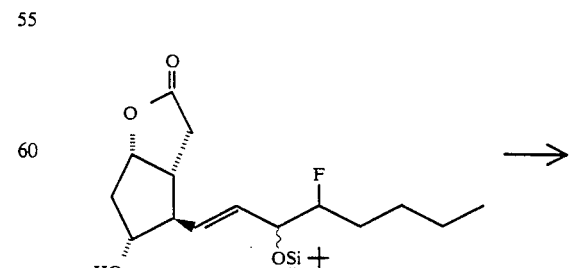

-continued
Preparation Chart II
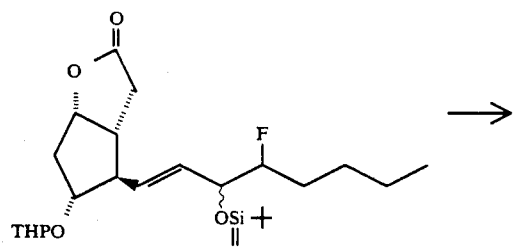
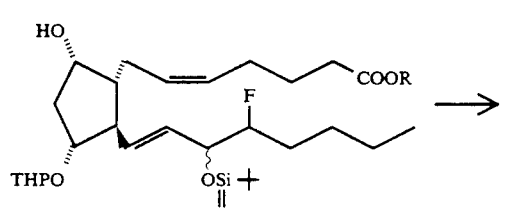
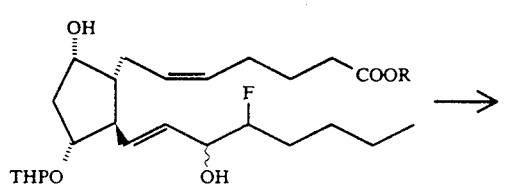
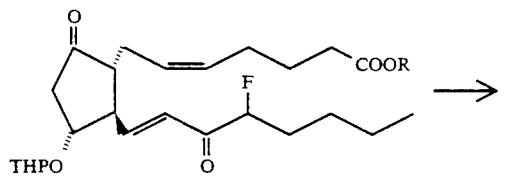
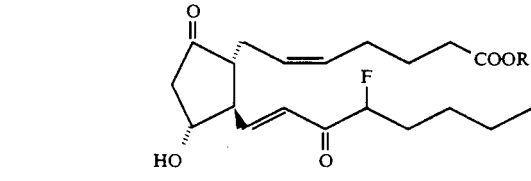
Preparation Chart III
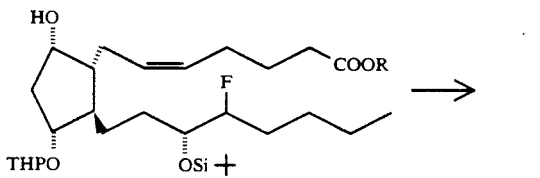
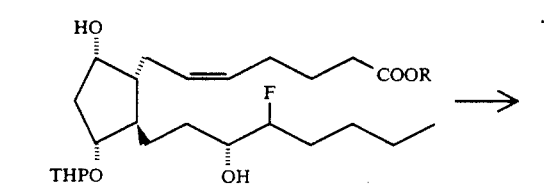
-continued
Preparation Chart III
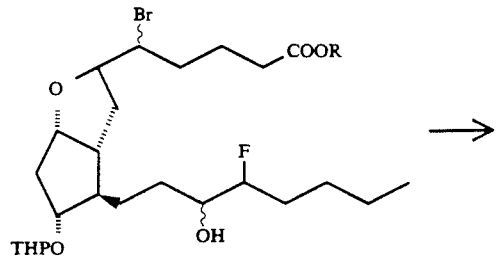
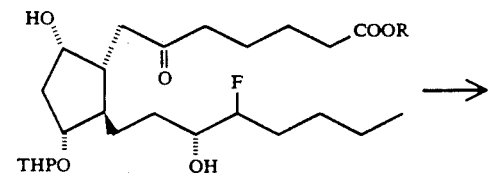
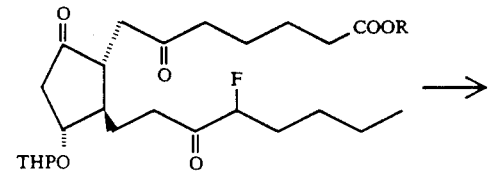
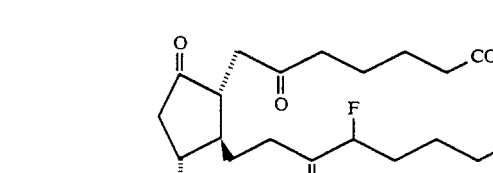
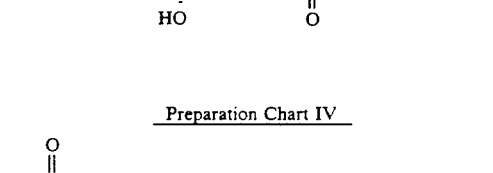
Preparation Chart IV
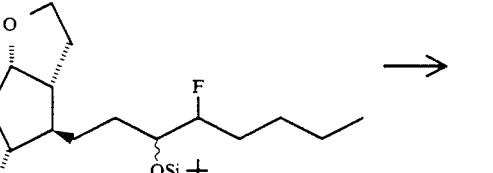
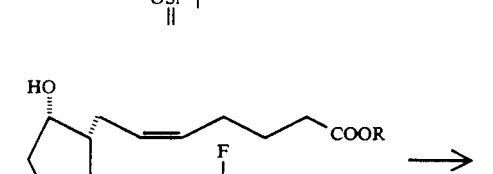
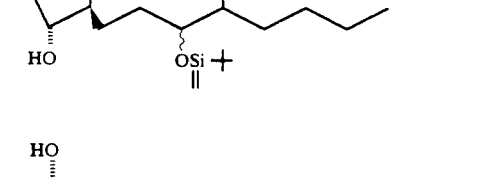

-continued
Preparation Chart IV

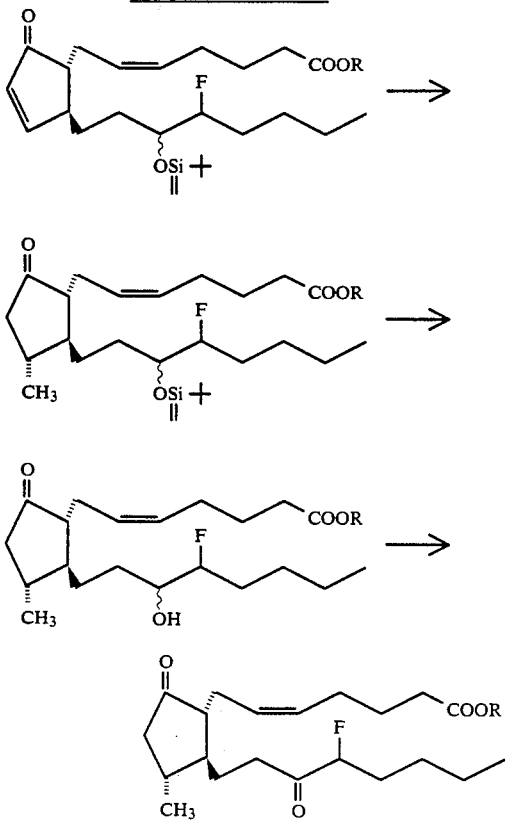

EXAMPLE 1

(Enteropooling effect)

Groups of five male rats (Crj Wister Rat; 180-240 g) were used. The test animals received only water, and 24 hours after abrosia. Subsequently, the test animals were received suspension of the test drug in distilled water (5 ml/kg). Thirty minutes after administration, they were killed by cervical dislocation and the average value of the intraintestinal content per animal was calculated after laparotomy, and expressed as a variation based on that of the control group (100%) and the dose which raised the intraintestinal content by 50% was referred to as ED50. The results are shown in Table 1.

EXAMPLE 2

(Intestinal contraction effect)

Ileum was enucleated from male rats (300-400 g) and suspended in Tyrode solution. The ileum was paused for 15-20 minutes until stabilized, and contracted several times with acetylcholine ($1 \times 10^{-6}$ g/ml). After two contractions with same intensity were obtained, the test drug was cumulatively administered at every 1 minute. The contraction caused by the drug was expressed as a variation based on that caused by acetylcholine ($1 \times 10^{-6}$ g/ml) (100%) and the concentration at which 50% contraction was caused is represented by $ED_{50}$. The results are shown in Table 1.

EXAMPLE 3

(Intestinal transportation ability)

Male Crj Wister rats (5-week old, 120-140 g) were used. The test animals fasted overnight, then the test drugs were orally administered to them. After 30 minutes, activated carbon (suspension in gum arabic) was orally administered. After 20 minutes, the animals were slaughtered and small intestine was enucleated. The full length of the small intestine (from pylorus to ileocecal) and the range of the transfer of the carbon powder were measured and transportation rate (%) was obtained.

Whether ransportation ratio of the group received the drug may be significantly promoted or not compared with that of the control group was examined. The results are shown in Table 1.

EXAMPLE 4

(Cathartic effect; rat)

Male Crj Wister rats (six-week old, 135-155 g) were used without fast. The animals were respectively placed in cages wherein sheets of paper were spread on the floor. The animals were observed without any treatment for first one hour then the animal discharged diarrheal feces were removed and the rest animals discharged normal solid feces were used.

The effect of the test drug was assessed at every 1-2 hours after the oral administration up to a maximum of 6 hours. The feces were assessed in such a way that solid feces which did not attached on the sheet of paper on the floor was regarded as normal feces while those attached to the sheet were regarded as diarrheal feces. And when at least one diarrheal feces were observed, the drug was evaluated to possess cathartic effect (+).

The results are shown as a ratio of the number of the animal discharging diarrheal feces to that of total animals used. According to this method, ED50 was calculated from the final cathartic efficacy. The results are shown in Table 1.

TABLE 1

| Test Drug | Entero-pooling $ED_{50}$ (mg/kg) | Intestinal Contraction* | Intestinal Transportation** | Cathartic Effect $ED_{50}$ (mg/kg) |
|---|---|---|---|---|
| 1 | 0.13 | + | − | >10 |
| 2 | 0.003 | ± | ++ | 0.8 |
| 3 | 0.002 | ± | ++ | 1.0 |

Also, the following test drugs 4 and 5 were tested using the procedure of Example 1, and the enteropooling ED50 (mg/kg) for compound 4 was found to be 0.0003 and that of compound 5 found to be 0.0007. Compounds 4 and 5 are set forth under "Test drugs" below.

*+: $EC_{50} < 10^{-6}$M
±: $10^{-6}$M ≦ $EC_{50}$ ≦ $10^{-4}$M
−: $EC_{50} > 10^{-4}$M
**−: No difference compared with the control group at the dose 10 mg/kg.
+: The transport ability of the test group significantly increased at the dose 1–10 mg/kg.
++: The transport ability of the test group significantly increased compared with the control gorup at the concentration lower than 1 mg/kg.
Test drugs:
1: Prostaglandin $E_2$
2: 13,14-dihydro-15-keto-16R,S-fluoro-prostaglandin $E_2$ methyl ester
3: 13,14-dihydro-15-keto-16R,S-fluoro-prostaglandin $E_2$
4: 13,14-dihydro-15-keto-16,16-difluoro-20-methyl-$PGE_2$
5: 13,14-dihydro-15-keto-20-ethyl-16,16-difluoro-$PGE_2$

EXAMPLE 5

(Cathartic effect; human)

Ten healthy male volunteers were employed and divided into two groups (5 men/group). One as test group was orally received coconut oil (200 μl) containing the test drug 2 (20 μg), while the other as control group received coconut oil (200 μl) alone.

As for test group, 4 out of 5 men complained of aerenterectasia and developed symptoms of loose or explosive diarrhea at 2-5 hours after administration. In this case, no one complained of other side effects such as bellyache and there found no abnormality according to the clinical observation. Further, at 8 hours after administration, no particular abnormality nor malaise in belly was observed for all volunteers including the above four men.

As for control group, there were nothing abnormal about all five men over the period of 8 hours after the administration.

EXAMPLE 6

Enteropooling effect (similar to Example 1) and intestinal contraction (similar to Example 2) were obtained for the following drugs. The results are shown in Table 2, 3 and 4.

TABLE 2

| Test drug | Enteropooling ED$_{50}$ (mg/kg) | Intestinal Contraction |
|---|---|---|
| 4 | 0.002 | ± |
| 5 | 0.002 | ± |
| 6 | 0.002 | ± |
| 7 | 0.002 | ± |
| 8 | 0.0002 | ± |

Test Drugs:
4: 13,14-dihydro-15-keto-16R,S-fluoro-PGE$_2$ ethyl ester
5: 13,14-dihydro-15-keto-16R,S-fluoro-20-methyl-PGE$_2$ methyl ester
6: 15-keto-16R,S-fluoro-PGE$_2$
7: 15-keto-16R,S-fluoro-PGE$_2$ methyl ester
8: 13,14-dihydro-15-keto-16,16-difluoro-PGE$_2$ methyl ester

TABLE 3

| Test Drug | Entero-pooling ED$_{50}$ (mg/kg) |
|---|---|
| 9 | 0.2 |
| 10 | 0.2 |
| 11 | 4.0 |

Test Drugs:
9: 13,14-dihydro-15-keto-16R,S-fluoro-Δ$^2$-PGA$_1$
10: 13,14-dihydro-15-keto-16R,S-fluoro-Δ$^2$-PGA$_1$ methyl ester
11: PGA$_1$

TABLE 4

| Test Drug | Entero-pooling ED$_{50}$ (mg/kg) | Intestinal Contraction |
|---|---|---|
| 12 | 0.20 | — |
| 13 | 0.14 | — |
| 14 | 0.20 | ± |
| 15 | 0.30 | ± |
| 16 | 0.70 | — |
| 17 | 0.60 | ± |
| 18 | 0.15 | — |
| 19 | 4.9 | + |

Test Drugs:
12: 13,14-dihydro-15-keto-16R,S-fluoro-PGF$_2\alpha$
13: 13,14-dihydro-15-keto-16R,S-fluoro-PGF$_2\alpha$ methyl ester
14: 13,14-dihydro-15-keto-16,16-difluoro-PGF$_2\alpha$ methyl ester
15: 13,14-dihydro-15-keto-16R,S-fluoro-20-methyl-PGF$_2\alpha$ methyl ester
16: 13,14-dihydro-15-keto-20-ethyl-16R,S-fluoro-PGF$_2\alpha$
17: 13,14-dihydro-15-keto-20-ethyl-16R,S-fluoro-PGF$_2\alpha$ methyl ester
18: 15-keto-16-R,S-fluoro-PGF$_2\alpha$ methyl ester
19: PGF$_2\alpha$ NMR and mass spectral data of the test drugs used in the examples will be shown below.
$^1$H NMR: R-90H manufactured by Hitachi, Ltd.
Solvent: CDCl$_3$
Mass: M-80B manufactured by Hitachi, Ltd.
EI: Ionization potential; 70 eV
SIMS: Ag plate-glycerin matrix (2)

δ: 0.73-1.06 (3H, m), 1.06-2.89 (23H, m), 3.63 (3H, s), 3.80-4.27 (1H, m), 4.44 (0.5H, m), 4.99 (0.5H, m) 5.36 (2H, m)
Mass(EI) m/z: 384, 366, 346, 335

(3)

δ: 0.73-1.05 (3H, m), 1.09-2.97 (22H, m), 4.08 (1H, m), 4.45 (0.5H, m), 5.00 (0.5H, m), 5.38 (2H, m), 4.88-6.88 (2H, brs) Mass(EI) m/z: 352 (M$^+$—H$_2$O), 282, 281, 226

(4)

δ: 0.73-1.05 (3H, m), 1.23 (3H, t, J=7Hz), 1.08-2.91 (23H, m), 4.08 (2H, q, J=7 Hz), 3.83-4.25 (1H, m), 4.44 (0.5H,m), 4.98 (0.5H, m), 5.35 (2H, m)
Mass(EI) m/z: 398 (M$^+$), 380 (M$^+$—H$_2$O), 226, 109, 95, 81

(5)

δ: 0.89 (3H, t, J=6 Hz), 1.10-2.88 (25H, m), 3.63 (3H, s), 3.81-4.26 (1H, m), 4.26-4.63 (0.5H, m), 4.99 (0.5H, m), 5.35 (2H, m)
Mass(EI) m/z: 398 (M$^+$), 380 (M$^+$—H$_2$O)

(6)

δ: 0.73-1.08 (3H, m), 1.14-3.21 (18H, m), 4.26 (1H, m), 4.58 (0.5H, m), 5.13 (0.5H, m), 5.35 (2H, m), 4.88-6.36 (2H, brs), 6.64 (1H, dd, J=16 Hz, J=3 Hz), 6.99 (1H, dd, J=16 Hz, J=8 Hz)
Mass(EI) m/z: 368 (M$^+$), 350 (M$^+$—H$_2$O), 330(M$^+$—H$_2$O—HF)

(7)

δ: 0.74-1.04 (3H, m), 1.13-2.95 (19H, m), 3.62 (3H, s), 4.23 (1H, m), 4.55 (0.5H, m), 5.10 (0.5H, m), 5.31 (2H, m), 6.60 (1H, ddd, J=15 Hz, J=3 Hz, J=1Hz), 6.94 (1H, dd, J=15 Hz, J=8 Hz)
Mass(EI) m/z: 382 (M$^+$), 351(M$^+$—CH$_3$O), 364(M$^+$—H$_2$O), 344 (M$^+$—H$_2$O—HF)

(8)

δ: 0.93 (3H, t, J=6 Hz), 1.08-2.75 (22H, m), 2.88 (1H, m), 3.63 (3H s), 3.81-4.33 (1H, m), 5.35 (2H, m)
Mass(EI) m/z: 402 (M$^+$), 384 (M$^+$—H$_2$O), 364 (M$^+$—H$_2$O—HF), 353 (M$^+$—H$_2$O-CH$_3$O)

(9)

δ: 0.75-1.05 (3H, m), 1.05-2.85 (24H, m), 4.43 (0.5H, m), 4.98 (0.5H,m), 5.77 (1H, d, J=16 Hz), 7.01(1H, dt, J=16 Hz, J=7.5 Hz), 7.50-9.30 (1H, brs)
Mass(EI) m/z: 354 (M$^+$), 336 (M$^+$—H$_2$O)

(10)

δ: 0.73-1.05 (3H, m), 1.05-2.82 (24H, m), 3.67 (3H, s), 4.43 (0.5H, m), 4.98 (0.5H, m), 5.76 (1H, d, J=16 Hz), 6.91 (1H, dt, J=16 Hz, J=7 Hz)
Mass(EI) m/z: 368 (M$^+$), 348(M$^+$—HF), 337 (M$^+$—CH$_3$O), 309 (M$^+$—COOCH$_3$), 269 (M$^+$—CH$_2$—CH=CH—COOCH$_3$)

(12)

δ: 0.73-1.05 (3H, m), 1.10-2.90 (22H, m), 3.87 (1H, m), 4.13 (1H, m), 4.43 (0.5H, m), 4.30-4.80 (3H, m), 4.98 (0.5H, m), 5.37 (2H, m)
Mass(EI) m/z: 372 (M$^+$), 354 (M$^+$—H$_2$O), 336, 284, 256

(13)

δ: 0.74–1.04 (3H, m), 1.07–2.86 (24H, m), 3.63 (3H, s), 3.85 (1H, m), 4.13 (1H, m), 4.43 (0.5H, m), 4.99 (0.5H, m), 5.39 (2H, m)

Mass(SIMS) m/z: 387 (M++1), 349 (M++1—H₂O)

(14)

δ0.92 (3H, t, J=6 Hz), 1.15–2.92 (24H, m), 3.63 (3H, s), 3.50–3.95 (1H, m), 4.17 (1H, m), 5.39 (2H, m)

Mass(EI) m/z: 404, 386, 368, 355

(15)

δ: 0.88 (3H, t, J=6 Hz), 1.15–2.90 (26H, m), 3.63 (3H, s), 3.87 (1H, m), 4.14 (1H, m), 4.43 (0.5H, m) 4.98 (0.5H, m), 5.39 (2H, m)

Mass(EI) m/z: 400, 382, 364, 362

(16)

δ: 0.87 (3H, t, J=6 Hz), 1.10–2.90 (26H, m), 3.87 (1H, m), 4.12 (1H, m), 4.43 (0.5H, m), 4.50–5.10 (3H, brs), 4.99 (0.5H, m), 5.38 (2H, m)

Mass(EI) m/z: 400 (M+), 382 (M+—H₂O), 362, 344

(17)

δ: 0.86–1.05 (3H, m), 1.15–2.75 (20H, m), 3.63 (3H, s), 3.90–4.33 (2H, m), 4.54 (0.5H, m), 5.11 (0.5H, m), 5.34 (2H, m), 6.52 (1H, dd, J=16 Hz, J=3.5 Hz), 6.91 (1H, dd, J=16 Hz, J=9 Hz)

Mass(EI) m/z: 384 (M+), 366 (M+—H₂O), 346 (M+—H₂O—HF), 303, 292

(18)

δ: 0.87 (3H, t, J=6 Hz), 1.15–2.90 (28H, m), 3.63 (3H, s), 3.86 (1H, m), 4.15 (1H, m), 4.45 (0.5H, m), 5.00 (0.5H, m), 5.40 (2H, m)

Mass(EI) m/z: 414(M+), 396 (M+—H₂O), 378, 358

Preferred subgroups of compounds herein are 13,14-dihydro-15-keto-16-mono or di-halo PGAs, PGEs and PGFs, including salts and esters thereof, especially, the PGE compounds. Preferably, halo is fluoro, i.e., PGEs as described in this paragraph where the 16-position is mono- or di-fluoro substituted. The PGE compounds can be PGE₁ or PGE₂ type. Other preferred compounds involved herein are of the above-noted type (13,14-dihydro-15-keto-16-mono or di-halo PGAs, PGEs and PGFs) wherein the 20-position is lower alkyl, preferably methyl or ethyl, substituted. Again, the more preferred compounds are of the PGE type with halo being fluoro.

Variations of the invention will be apparent to one of ordinary skill in the art.

What is claimed is:

1. A process for providing a cathartic effect to a patient in need thereof which comprises administering to cathartic-inducing effective amount of a 15-keto-16-halogen PGA, PGE or PGF having the following skeleton:

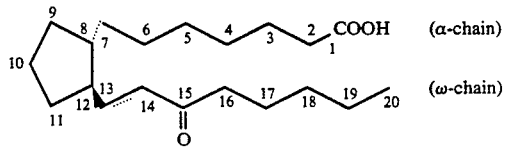

and wherein said skeleton is saturated or contains at least one unsaturated bond which is a 2,3-, 5-6- or 17,18-double bond or a 5,6- triple bond, and is not further substituted or is further substituted at at least one of C-3, C-6, C-17, C-19 and C-20 positions of the skeleton by a halogen atom, an alkyl group, an alkoxy group, a carbonyl group, a hydroxyl group, a phenyl group or a phenoxy group, or a pharmaceutically acceptable 1-ester or salt thereof, and a pharmaceutically acceptable carrier.

2. The process of claim 1, wherein said halogen atom is a fluorine, chlorine or bromine atom.

3. The process of claim 1, wherein said alkyl group is methyl, ethyl, isopropyl or isopropenyl group.

4. The process of claim 1, wherein said alkoxy group is methoxy or ethoxy group.

5. The process of claim 3, wherein said alkyl group is at the C-3, C-17 or C-19 position.

6. The process of claim 1, wherein said carbonyl group is at the C-6 position.

7. The process of claim 1, wherein said alkyl or alkoxy group is at the C-20 position.

* * * * *